United States Patent [19]

Kovach

[11] Patent Number: 5,395,623
[45] Date of Patent: Mar. 7, 1995

[54] HUMAN FOOD PRODUCT DERIVED FROM CEREAL GRAINS AND PROCESS

[75] Inventor: Nickolas C. Kovach, Kansas City, Mo.

[73] Assignee: Cereal Ingredients, Inc., Kansas City, Mo.

[21] Appl. No.: 40,723

[22] Filed: Apr. 1, 1993

[51] Int. Cl.⁶ .............................................. A23L 1/09
[52] U.S. Cl. ...................................... 426/28; 426/20; 426/21; 426/64; 426/455; 426/456; 426/463; 426/465; 426/466
[58] Field of Search ........................ 426/28, 20, 21, 49, 426/64, 455, 456, 463, 465, 466

[56] References Cited

U.S. PATENT DOCUMENTS

| | | | |
|---|---|---|---|
| 3,014,802 | 12/1961 | Hellman et al. | 426/28 |
| 3,689,277 | 9/1972 | Sfat et al. | 426/28 |
| 5,061,497 | 10/1991 | Thacker et al. | 426/31 |

FOREIGN PATENT DOCUMENTS 0231729 2/1986 European Pat. Off. .

Primary Examiner—Helen Pratt
Attorney, Agent, or Firm—Harold D. Jastram; Robert A. Elwell

[57] ABSTRACT

A bakery ingredient including a milled, starch-bearing grain having about 60–80% of its starch enzymatically eliminated by conversion to a soluble form and about 4 to 30% by weight of a caramel-sugar mixture is disclosed along with a process for preparation of the bakery ingredient. The preferred sugar mixture includes at least 70% maltose and less than 5% glucose. The preferred enzyme is an alpha-amylase. Baked goods prepared from the bakery ingredient demonstrate superior crumb strength and are suprisingly resistant to degradation by excessive or insufficient moisture and are characterized by extended shelf-life capability.

24 Claims, 1 Drawing Sheet

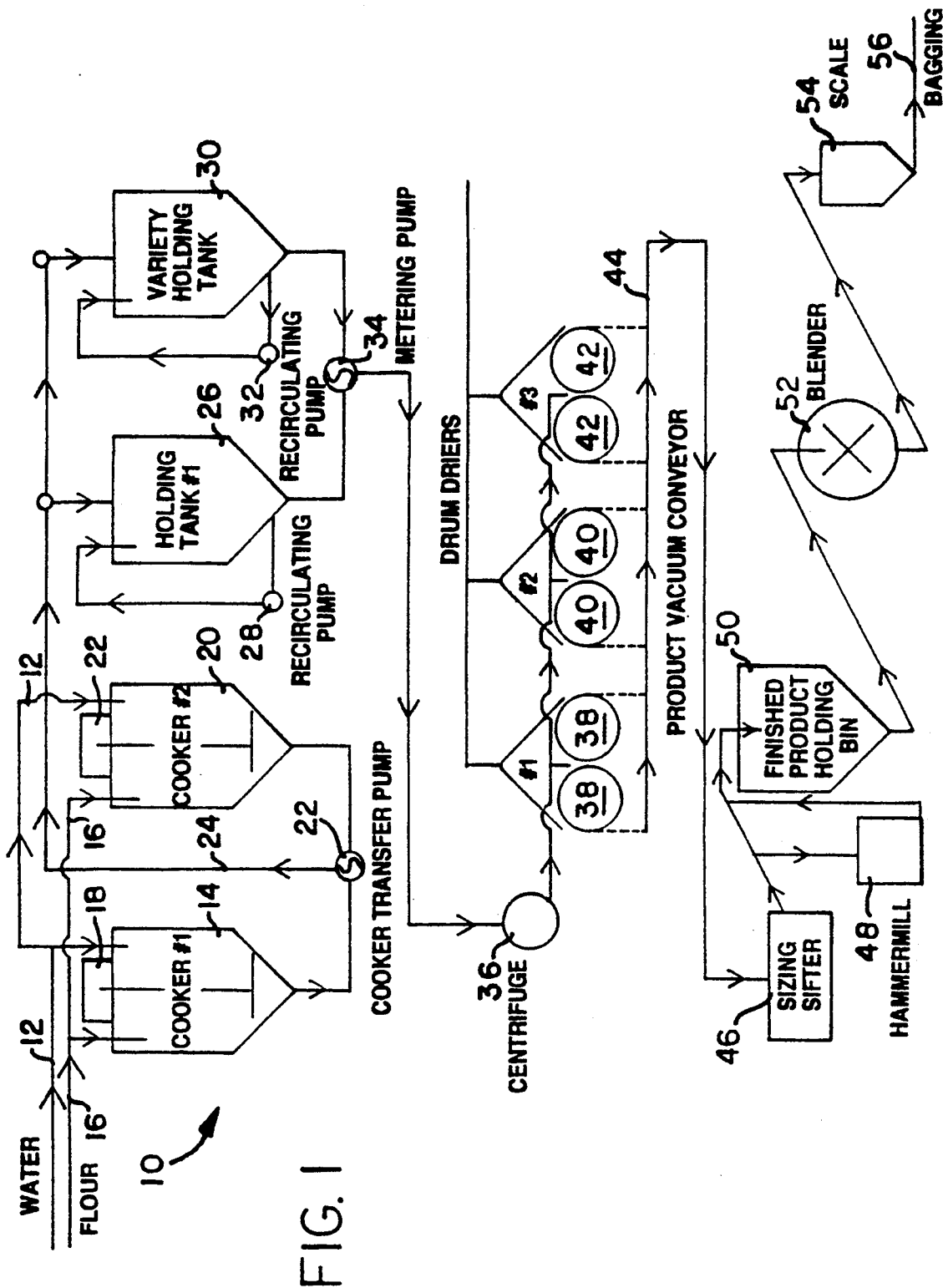

HUMAN FOOD PRODUCT DERIVED FROM CEREAL GRAINS AND PROCESS

The products and processes of the present invention relate to human food products derived from cereal grains, and in particular, relate to high-fiber, high-protein, reduced-starch human food products which are in part prepared through enzymatic treatment of cereal grains.

BACKGROUND OF THE INVENTION

A particularly desirable product for the baking industry would be a consumer product having reduced calories. It would also be desirable to have a consumer product having increased dietary fiber and increased proteins relative to typical baked consumer products. Unfortunately, most attempts, to prepare such products have been less than fully acceptable to consumers. Specifically, the drawbacks of the present reduced calorie or high-fiber bakery products have been short shelf life and poor crumb quality within such baked product. The preparation of such products has relied upon the addition of atypical bakery ingredients. For example, one atypical bakery ingredient used to increase the dietary fiber of the final product is oat fiber. Oat fiber, however, does not produce a particularly acceptable consumer product nor does it constitute significant protein. The use of bi-products of ethanol production, such as distillers dried grains and brewers spent grain, have been known for years as suitable animal food products. More recently, attempts to modify the traditional processing of starch from cereal grains to provide both an economical feed stock for alcohol production and a more useful by-product have met with mixed success. For a discussion for the use of distillers dried and brewers spent grains in human food, see U.S. Pat. No. 4,828,846 to Rasco, et al which is hereby incorporated by reference. The Rasco patent process modifies the traditional treatment of cereal grain in order to achieve a more palatable by-product after fermentation. It should be particularly emphasized that in the Rasco process, the by-product is exposed to the alcohol produced by yeast during fermentation.

European Patent Application No. 231,729 by Bergkvist, et al discloses sweet syrup production from cereal grains treated with alpha-amylase. Note that the objective in the Bergkvist disclosure is the maximization of sugar syrup production from the grain.

The Thacker, et al patents, U.S. Pat. Nos. 5,061,497 and 5,106,634, both also incorporated by reference herein, disclose the exhaustive enzymatic solubilization of the starch portion of grain by alpha-amylase and centrifugation of the reduced starch grain residue away from the solubilized starch solution prior to fermentation. A portion of the solubilized starch solution remains with the solid grain residue and upon drying becomes a coating on the residue. The coating tends to improve the organoleptic properties of the residue and therefore enhances its usefulness in the food industry, particularly the baking industry. Thacker recommended drying at a non-scorching temperature preferably below 75° C. (167° F.). Unfortunately, although the dried product may be used in baking, the process details of the Thacker invention result in a quality control problem. For that reason, the dried product tends to be highly variable and allows for considerable improvement in quality and consistency. Even the best product of the Thacker process provides only a moderate achievement of the desired goal of a low calorie, high-fiber, high quality baked consumer product.

It would be particularly useful to further advance over the organoleptic properties of the Thacker-type products. In the invention described subsequently, advances in selection of the sugar solution composition resulting from the enzymatic degradation, processing, and heat treatment allows major advances in the baking industry.

SUMMARY OF THE INVENTION

In a first embodiment, the present invention is a baking ingredient including first, a milled, starch-bearing cereal grain having about 60–80% of the starch enzymatically converted to a soluble form, and second, about 4–30% by weight of a caramel-sugar mixture. The sugars of said caramel-sugar mixture include at least 70% maltose and less than 5% glucose. The preferred starch-bearing cereal grain is wheat. The preferred enzyme preparation for the enzymatic conversion is alpha-amylase, most especially alpha-amylase from a bacterial source most particularly alpha-amylase produced by submerged fermentation of a selected strain of *Bacillus amylolichuefaxiens*, systematic name is 1,4-alpha-D-glucan glucano-hydrolase (EC 3.2.1.1.) such as for example the enzyme product available as BAN from NOVO Nordisk Bioindustrials, Inc. of Danbury, Conn. Such an enzyme preparation is substantially free of maltase activity. The alpha-amylase or other selected enzyme is thermally denatured when 60–80%, preferably 70–75%, of the starch is converted to soluble form and eliminated from the milled grain. The remaining solid portion of the grain will be occasionally referred to herein after as a "vestige". The resulting preferred product, when dried, is characterized by a protein content of about 26–30% and a total dietary fiber content of about 32–35%. In a most preferred embodiment, the source of the sugar and the caramel is the solubilized starch. The caramel is generated in a heating step, in which about 30–50% of the sugar is caramelized and the entire product is dried to about 2–9%, preferably 3–4% moisture content, as will later be explained. Another characteristic of the preferred ingredient is that it is substantially free of crystals of sugar of a size capable of mechanically damaging a yeast-raised dough. By way of background, yeast-raised products such as, for example, bread dough, yeast-raised donuts, hamburger buns, English muffins, are susceptible to mechanical laceration of gluten strands, whereas chemically leavened products such as cakes, cookies, crackers and pancakes are relatively immune to the detrimental effects of sugar crystals.

In another embodiment, the baking ingredient of the present invention can be mixed with starch or flour to form a baking premix. Typically, the preferred embodiment baking ingredient (i.e. a vestige of wheat origin with 70–75% of the starch removed and a caramel-maltose portion) would be mixed at a rate of 15.5 kg (34 lbs) of the baking ingredient for every 45.5 kg (100 lbs) of flour. In yet another embodiment, the present invention is a baked good for human consumption prepared from a dough including the bakery ingredient of the present invention. Such a baked good is characterized by increased fiber and protein and decreased calories relative to typical bakery goods. Such baked goods also demonstrate superior crumb strength relative to comparable commercial high-fiber low calorie baked goods. Remarkably, baked goods of the present invention are surprisingly resistant to degradation by excessive or insufficient moisture. This resistance is most noticeable as extended shelf life capability.

The present invention also includes a process for preparing a bakery ingredient. The process includes the steps of:
- suspending a milled grain in aqueous media;
- enzymatically solubilizing a substantial portion of the starch of the milled grain;
- terminating the enzymatic solubilization of starch when between about 60–80% of the original starch of the milled grain is solubilized;
- separating the suspended starch depleted milled grain from a substantial fraction of the aqueous media incorporating solubilized starch; and
- heating the separated grain in the presence of the remaining fraction of the aqueous media incorporating solubilized starch.

Preferably, the heating step occurs at a temperature and for a time sufficient to caramelize a portion of the solubilized starch and preferably the heating step results in a product with a moisture content of between about 2–9% moisture. Most preferably, the step of enzymatically solubilizing the starch includes exposure to alpha-amylase and the heating step causes the production of maltose and the heating step results in caramelization of from about 30% to about 50% of the maltose in the remaining fraction of the aqueous media incorporating the maltose. Preferably, the enzymatic solubilizing step involving alpha-amylase causes the production of a sugar profile or sugar composition with more than about 90% maltose and less than about 5% glucose.

Additionally, in the preferred process, the suspension of milled grain is mixed or agitated prior to the separation step to provide a substantially homogeneous separated grain in the presence of remaining fraction of aqueous media incorporating solubilized starch for the heating step. In the preferred process, the dried product resulting from the heating step is blended, in order to avoid separation of fines.

In another aspect of the preferred process, an enzyme preparation is selected to convert the starch of the milled grain to a preselected sugar composition. In the preferred embodiment, the preselected sugar is maltose, however, the process could be used to convert the starch to other sugars such as fructose. Because fructose has different properties than maltose or glucose, it is envisioned that a fructose or other sugar composition might be useful in other food products, such as meat based products, vegetable based products, or dairy based products. In yet another embodiment of the present invention, the present invention includes a baking ingredient including milled, starch-bearing cereal grain having about 60–80% of the starch enzymatically eliminated and converted to a pre-selected sugar composition, and a mixture of caramel and the pre-selected sugar composition.

Additionally, the present invention includes a high-fiber and protein food product including a particle consisting essentially of the vestige of alpha-amylase digested, gelatinized, milled, starch-bearing cereal grain and an intimately associated portion consisting essentially of partially caramelized maltose. Further, the present invention includes a food including a vestige of milled, starch-bearing cereal grain enzymatically treated to solubilize 60–80% of the original starch. The cereal grain may be selected from amongst wheat, corn, pearled barley, psyllium, millet, rice, rye, sorghum, oats, or combinations thereof.

BRIEF DESCRIPTION OF THE DRAWINGS

FIG. 1 is a schematic illustration of the apparatus used to perform the process of the present invention.

DETAILED DESCRIPTION OF THE PREFERRED EMBODIMENTS

A preferred embodiment of the process of the present invention, can perhaps be best explained with reference to FIG. 1. The overall apparatus and process is depicted schematically at 10 of FIG. 1 and can be thought of as sequentially processing through cooking and enzymatic treatment, liquid solid separation, heat treatment and dry handling and blending. In a preferred embodiment cooking and enzymatic treatment are batch processes and subsequent steps are continuous processes, thereby leading to increased consistency in dried product.

Cooking

In the cooking step, the cooker 14 is initially charged with water. The agitator 18, or stirring mechanism, is then activated. Next, milled grain, (i.e. flour or grain ground to a substantially uniform size to pass through a 0.25 mm screen (60 mesh)), is charged into the cooker until the flour has been mixed with the water within the cooker 14.

Milled grain may consist of wheat, corn, pearled barley, psyllium, millet, rice, rye, sorghum, oats, or other starch-bearing grain, either alone or in combination. The preferred grain is the wheat kernel. Typically, the slurry formed between the water and ground grain has a solids content from between 20 to 50 percent. Varying the solids concentration may be used as a control method to vary the sugar concentration in the liquid portion and, ultimately, the sugar portion of the final product.

Water is input through pipe 12 into cooker 14. Flour is input through pipe 16 into cooker 14. Cooker 14 includes a stirring mechanism 18 and is connected to a boiler (not shown) such that the slurry created between the flour and the water may be heated to a desired temperature while continuously stirred. Similar cooker 20 with stirring apparatus 22 is also connected to flour lines 16 and water lines 12 and may be operated in parallel or alternated with first cooker 14.

Suitable steam is then applied to the flour water mixture. The temperature is raised to approximately 32° C. (90° F.). This temperature change takes roughly half an hour. As the temperature reaches approximately 32° C. (90° F.) in the mixture or slurry, enzyme is added to the mixture. Preferably, the enzyme is an alpha-amylase enzyme and is typically added at an amount of approximately 0.12% of the weight of the flour within the slurry. Most preferably, the alpha-amylase enzyme produces a high concentration of maltose. Most preferably, alpha-amylase produced by a submerged fermentation of *Bacillus amylolichuefaciens*, systematic name 1,4-alpha-D-glucan glucano-hydrolase (EC 3.2.1.1) which is an endo-amylase hydrolyzing 1,4-alpha-glucosidic linkages at random and producing breakdown products of dextrins and oligo-saccharides and maltose. One source of most preferred enzyme is the bacterial alpha-amylase supplied under the name BAN from Novo Nordisk Bioindustrials, Inc. of Danbury, Conn., particularly, 120 KNU/g, where 1 KNU is the amount of enzyme the breaks down 5.26 grams of starch per hour in the presence of 0.0043 molar calcium at 37° C., pH 5.6 and a 7-20 minute reaction time. The absence of maltase enzyme is highly desirable as high glucose concentrations are believed undesirable in the end product. After the enzyme has been added, the temperature is raised to about 189° C. (204° F.). The change in temperature takes approximately 30 to 40 minutes. While the temperature is being raised, the starch portion of the flour gelatinizes. The gelatinization of the starch is detected by a dramatic increase in viscosity. This serves to open up the starch structure and provide improved access of the enzyme to the starch structure. In turn, the gelatinization allows the enzyme (preferably alpha-amylase) to effectively and efficiently "clip" or hydrolyze starch molecules into smaller sub-units which are soluble and thus liberated from the flour. Gelatinization for wheat flour typically occurs in the range of 77° C. to 99° C. (170° to 210° F.). A temperature of about 96° C. (204° F.) is the preferred temperature. Once the starch of the flour has been gelatinized, the enzymatic degradation of the starch begins. It is relatively time critical that not more than 1 to 1½ hours and preferably 30 to 45 minutes be allowed for the enzymatic degradation of a major portion of the gelatinized starch of the flour to occur. Of course, one of ordinary skill in the art will recognize that the ratio of enzyme to substrate and time are critically inter-related. A critical feature of this enzymatic degradation step is that not all of the starch of the flour is degraded and solubilized. Specifically, sufficient time and enzyme and temperature are allowed to achieve between 55 to 80%, preferably 65 and 75% of the total original starch being removed from the product. Thus, on the order of at least 20% of the starch is left in the flour particles. Exhaustive enzymatic digestion should be avoided. Exceeding this limitation of the enzymatic degradation allows for some loss of quality in the fiber as well as some potential loss of protein. It is highly critical that at least 20% of the starch remain unsolubilized or unremoved from the flour.

As will be explained subsequently, the termination of the enzymatic reaction by increase in temperature (or alternative enzyme denaturing processes such as pH denaturation) at the appropriate point in time results in the preferred residual starch amount in the final product 07 from 12 to 20% and most preferably, about 16% of the final dried packaged product, as residual starch. Typically, initially between 70 and 80% of the wheat flour charged into the slurry was starch. After the temperature in the slurry has reached about 96° C. (204° F.) which should take approximately 30 or 40 minutes, the Brix value of the solution should be checked. The Brix reading should be approximately 15 to 15.5 which is indicative of the sugar content of a liquid solution. The temperature should be held at about 96° C. (204°) for about 15 minutes, then transferred. The Brix content should again be checked at transfer. It should also be noted that the holding tanks are unheated.

Liquid Solid Separation

Slurries from cooker 14 and cooker 20 are moved from the bottoms of the cookers through cooker transfer pump 22, then through slurry line 24 for placement in holding tank 26. A recirculating pump 28 draws from adjacent the bottom of holding tank 26 and returns into the top of holding tank 26 to allow for mixing of the slurry in order to prevent separation and settling of the slurry and retain homogeneity within the slurry. A similar vessel which may be used for holding varieties or used an additional holding tank 30 also includes a recirculating pump 32 to maintain the slurry in appropriate suspension by removal of slurry from adjacent the bottom of the holding tank 30 and replacement into the top of holding tank 30. During the residence time in the holding tank, the recirculating pump 28 serves to take slurry from the bottom of the holding tank and replace it into the top of holding tank 26 at a rate of approximately one tank volume every four minutes. This serves to maintain uniformity and keep the suspension homogeneous. Without the recirculating pump 28, and system there is a significant tendency of the slurry to begin to settle out or stratify within the holding tank 26. These effects are detrimental because they cause variations in centrifuge output (cake) quality which in turn results in variations when heated.

In order to separate out the excess liquid from the desirable solids of the slurry, the centrifuge should be started, preferably at the rate of about 900 rpm. Contents of the holding tanks 26 and 30 are selectively removed through a metering pump 34 for transfer to centrifuge 36. The metering pump 34 is set to provide constant solids input to the centrifuge 36 as opposed to constant volume. In combination with the recirculating pumps 28 or 32 of the holding tanks 26 and 30, respectively, the metering pump and homogeneous suspensions provide a consistent slurry feed to the centrifuge 36. Additionally, the conveyors and drums for the drying system should be turned on in order to accept the product from the centrifuge 36. The metering pump 34 between the holding tank 26 and the centrifuge 6 should be started at approximately 50 lb. per minute and slowly increased to 150 lb. per minute. The combination of the metering pump 34 and the recirculating pump 28 for holding tank 26 provide a uniform and dependable feed of slurry to the centrifuge 36. Experience has shown that this combination of uniform homogeneous slurry is required to provide a consistent cake quality from the centrifuge 36 to appropriately feed the drum dryers 38, 40 and 42. The centrifuge is a Byrd HB 194 and is operated at between 1800 and 3400 rpm and most preferably between 1800 and 2200 rpm. The processing time is about 1 to 4 minutes, preferably 2 to 3 minutes. Supernatant liquid may be sent to waste or alternatively sent to a storage facility (not shown) for further processing into alcohol or sugar. The cake or solids portion, including a small portion of the liquid which was not completely separated by the centrifuge is then transferred to drum dryers shown in this example as 38, 40 and 42. It should be noted that the critical control factor is the liquid/solids ratio in the product coming out of the centrifuge. Preferably, the solids from the centrifuge 36 being applied to the drum dryers 38, 40 and 42 should have a moisture content of not more than approximately 60% and a solids content of not less than approximately 40% (most preferably 40-60% solids) and most especially preferred is a solids content of about 50%.

Heat Treatment

The high solids product cake from centrifuge 36 is next applied to the drum dryers. The drum dryers are approximately 60 inch diameter drums circulating at 1-3 rpm, preferably approximately 2 rpm. The material applied to the drum surface has a dwell time (over about ¾ of a revolution of the drum) of approximately 24 seconds. The internal temperature of the drying drums is about 177° C. (350° F.) (supplied by steam from a boiler) providing an external surface temperature of approximately 154° C. to 160° C. (310° F. to 320° F). Because a small portion of the liquid solution remains with the solids after centrifugation, this solution contains sugars and other starch solubilization products remaining from the enzymatic removal of the starch from the cereal grain. Applying this mixture of sugar-containing liquid and solids to the hot surface of the drum dryers causes a removal of water as steam and additionally, depending upon the temperature and the particular sugars present in the liquid, will cause some caramelization of the sugars. For example, sucrose begins to boil and caramelize at a temperature about 141° C. (286° F.). Glucose begins to boil and caramelize at a temperature of about 158° C. (317° F.). The end result, after approximately 24 seconds of exposure to the hot drum surface, is a partially caramelized sugar combined with the vestiges of flour particles, less the removed starch. This vestige of the flour particle, created by the enzymatic treatment, becomes dried together with the dissolved solids and newly formed caramel from the liquid portion of the cake of the centrifuge. By appropriate selection of temperatures and sugars within the solution, it is possible to minimize the crystallization of sugar, most particularly avoiding large crystals and generating a fairly amorphous or glass-like material of previously dissolved solids in combination with the cereal grain vestige. The thus treated product is scraped from the drum as flakes. The product of the drum dryers 38, 40 and 42 is received by the vacuum conveyor 44. At this stage, moisture content of the product is 2-9%, preferably about 3 to 4%. A moisture content of 6% is acceptable, however, a moisture content in the range of 10% indicates that too much moisture is present in the product and a short shelf life will be expected such that a baker would have to rapidly incorporate this ingredient into a baked product rather than holding it for a number of days or weeks. Alternatively, at extremely low moisture contents, such as for example, below 2% moisture excessive caramelization of sugars may have occurred. This is also particularly wasteful of energy since additional energy is being used to decrease the moisture content below about 3% moisture. Additionally, excessive drying, that is below 2% moisture tends to be characterized by a higher amount of crystallization of the sugars. Sugar crystals tend to mechanically cut or disrupt gluten fibers in yeast-raised dough which may be prepared from the dried product and therefore, are detrimental and should be avoided in the final dried product.

Dry Handling/Blending

The dried product from the vacuum conveyor 44 is delivered to the sizing sifter 46. The sizing sifter separates product of appropriate size which is #4 mesh size (approximately 6 mm). Portions of product exceeding the desired screen size travel into hammer mill 48 where they are reduced in size and redeposited in the sizing sifter and rejoin the main product stream. From the sizing sifter, the product is deposited in a holding bin 50. Prior to packaging, the product from the product holding bin 50 is processed through a blender 52 which serves to further increase the uniformity of the product and prevent fines from separating. Finally, the product is sent to a scale 54 and then bagging unit 56. Blender 52 holds approximately 300 to 350 pounds of product. In bagging, the product is placed in 3-ply bags, the bags are then sewed shut and placed on pallets. Moisture check of the finished product at this stage should be less than 6% moisture.

Having now briefly described the apparatus in which the process is performed, it will be possible to discuss in greater detail the various process steps of the present invention.

Enzymne/Sugar Selection/Caramelization

Another significant aspect of the present invention is the selection of an enzyme providing the desired sugar compositions in the liquid. The preferred enzyme is an alpha-amylase, particularly an alpha-amylase which will produce a high concentration of maltose. Most preferably, the enzyme preparation should be alpha-amylase produced by a submerged fermentation of *Bacillus amylolichuefaciens*, systematic name 1,4-alpha-D-glucan glucano-hydrolase (EC 3.2.1.1) which is an endo-amylase hydrolyzing 1,4-alpha-glucosidic linkages at random and producing breakdown products of dextrins and oligo-saccharides and maltose. One source of most preferred enzyme is the bacterial alpha-amylase supplied under the name BAN from Novo Nordisk Bioindustrials, Inc. of Danbury, Conn., particularly, 120 KNU/g, where 1 KNU is the amount of enzyme the breaks down 5.26 grams of starch per hour in the presence of 0.0043 molar calcium at 37° C., pH 5.6 and a 7-20 minute reaction time. This particular enzyme is of bacterial origin and in the present system yields approximately 94.5 percent of the total sugar in the supernatant as maltose.

The high maltose concentration is important from the baker's viewpoint. Maltose, in the baking industry appears to have two competing affects. First, maltose in concentrations above about 1% is believed to be detrimental to the bread dough, specifically, it tends to interfere with the appropriate functioning of the gluten in flour. This, in turn, tends to result in a loss of "crumb strength" after about two days in a bakery product. High maltose helps dough "relax" and improves "machine-ability." By "machine-ability," is meant, the ability to handle dough in industrial baking machinery which provide mechanical processes such as kneading, cutting into loaves, separation from pans, and extrusion. The dried product of the present invention, that is the product in bags at bagging unit 56, might be expected to contain approximately 12 to 18 percent maltose, preferably about 16% maltose. However, due to caramelization of 30-50% of maltose, contains almost 6-12% maltose. When this product is used in the preparation of bread or other bakery products, it is often combined in a ratio of 15.5 kg (34 lbs) of the dried product to about 45.5 kg (100 lbs) of flour. This provides mixtures of yeast-raised dough which might be expected to include about 4% maltose on a dried basis, however, due to caramelization (as explained below) this is reduced to about 2-3% maltose, on a dried basis, in yeast-raised dough.

This exceptionally high concentration of maltose in the resulting yeast-raised dough is believed by the inventor to be effective because the maltose becomes pre-dispersed throughout the flour while still in a dried state as attached to the dried product from the bagging station 56. This pre-dispersion of maltose in a dried state and possibly a slower release of the maltose from the dried product of the present invention avoids detrimental effects expected from high maltose concentrations and allows for a higher maltose concentration in the final dough. This, in turn, aids in achieving excellent machine ability in a dough prepared with the dried product of the present invention. The resulting bakery products incorporating the dried product do not suffer from the loss of "crumb strength" after about two days. Rather baked products incorporating the dried product tend to be characterized by extended shelf lives of on the order of ten days.

Another aspect of the high maltose concentration in the dried product, is the effect of heating on the drum dryers 38, 40 and 42. It is believed that the drum dryers cause a significant caramelization, on the order of 30–50% of the maltose and 40 to 60 percent of the total sugar, which is approximately 94% maltose in the product. Thus, total maltose in the bread dough is approximately 2%–3% on a dried-weight basis. This is roughly twice to triple the amount which would be expected to be used within the baking industry.

The caramelized portion of the sugars in the dried product also tend to be of particular significance within the baking industry. Specifically, as the moisture content of the cake from the centrifuge 36 is driven off by the hot surfaces of the drum dryers 38, 40 and 42, some water is chemically eliminated from the maltose and results in caramelization. It is estimated by the inventor that approximately 30% to 50% of the maltose is caramelized during the exposure to the drum surface during a 24 second exposure to about 310° F. to 320° F. surface and that presumably the glucose and fructose portions of the total sugars are caramelized in advance of the caramelization of the maltose. As is well known, caramelized sugars tend to be flavors and color rather than sweeteners and are highly soluble. Once the dough has been formed, the caramelized sugar tends to dissolve throughout the dough. Additionally, caramel has been difficult to provide and use in bread doughs, however, it is well known to provide desirable flavor within finished bakery products. The present invention enables a baker to employ caramelized flavor within a bakery dough to provide a final product with incorporated caramel. The incorporation of caramel within a bakery product tends to save energy since the appearance of the final product, that is, a desirable darkened color, is achieved with less energy and less baking time. Additionally, reduced baking time tends to result in reduced degradation of flavors within the final bakery product.

Another aspect of the dried product of the present invention is its ability to serve as a reservoir or buffer of moisture within the final bakery product. The inventor believes that this is a newly recognized property of a cereal grain vestige. The reservoir or buffer effect towards moisture is best understood in light of the example of a cinnamon roll prepared from a dough employing the present invention. Traditional cinnamon rolls are initially prepared by rolling a flat sheet of dough which has been treated with a layer of cinnamon paste and then slicing into small cylindrical portions in advance of baking. The baked product produced from such rolled dough initially tends to appear as a tightly wound roll. However, upon a relatively brief aging period of on the order of a few days, the reduction in volume of the baked dough begins to cause the cinnamon roll to appear loose and one may even be able to see complete separation between the various wound layers of the roll. At this point, the product becomes unacceptable to consumers. Cinnamon rolls prepared using the product of the present invention in the dough demonstrate a shelf life of on the order of about 10 days as compared to the typical two or three days for traditional cinnamon rolls. The inventor theorizes that in this situation, the product of this invention has served as a reservoir of moisture for the bakery product and provides, as needed, sufficient, moisture to delay the drying out and aging of the baked product thereby extending the shelf life.

Another example, a bakery roll which is used to prepare a sandwich filled with a hot, moist ingredient, then wrapped with a relatively moisture impervious cover tends to demonstrate a degradation of the bakery product adjacent the impervious covering. It is believed that degradation is due to the migration of moisture from the warm moist filling toward the relatively cooler portion of the bakery product adjacent the impervious moisture and a condensation-like effect within the bakery product. This condensation effect tends to produce a soggy area which leads the entire bakery product and sandwich to be unacceptable to consumers. A similar roll prepared with the product of this invention and prepared as a sandwich incorporating a hot, moist filling and a similar impervious barrier wrapped about the sandwich, tends to not demonstrate the soggy degradation of the bakery product. It is believed by the inventor that the vestige of cereal grain absorbs the excess moisture in such circumstances. Thus, the product of this invention enables the preparation of hot bakery products incorporating a hot moist filling and wrapped within an impervious coverage retain their consumer desirability for a much greater period of time.

Additional uses for the product of the present invention include preparation of low-fat, high-fat fiber cookies; water-based cinnamon fillings for low/no-fat sweet goods; pizza crust, English muffins, bran muffins, and as an extender or fat reducer for meat products. Additionally, the product may be used to prepare breads and buns; crackers; cookies; sweet goods; cake products; cereal; baking mixes; pancake mixes; English muffins; breading mixes; and candies.

EXAMPLE ONE

Three Thousand One Hundred Eighty (3,180) gallons of water was placed within cooker 1. While agitation was provided, over a period of about 25 minutes, 9,000 pounds of flour was added to cooker 1. Steam from a boiler at about 120 psi was applied to the cooker to slowly increase the temperature over a 30 minute period to about 32° C. (90° F.). 4.9 kg (10.8 lbs) of enzyme (0.12% of the flour) (BAN 120L brand alpha-amylase from NOVO). Next, over a 30 to 40 minute period the temperature was increased to about 96° C. (204° F.) by additional application of steam. At about 96° C. (204° F.), Brix was tested and observed as between 15 and 15.5. While agitation continued, the temperature was maintained at about 204° F. for 15 minutes. After the 15 minute period, the solution was transferred to the holding tank. The recirculating pump was applied to the holding tank. Next, the centrifuge was operated with an initial rotational rate of 900 rpm, and then slowly increased as the slurry was fed to the centrifuge at 1200 to 1600 rpm. Next, the conveyors and drums were started and the metering pump to the centrifuge to the holding tank was initiated at 22.7 kg (50 lbs) per minute gradually increasing to 68 kg (150 lbs) per minute. After 1 to 3 minutes, the cake from the centrifuge begins to be applied to the surface of the drum dryers. After leaving the drum dryers, the product is vacuumed through the cyclone sifter and up to the blender. The product was then blended and bagged, the bags sewed and placed on pallets. Moisture check of the finished product is taken immediately before bagging and showed less than 6% moisture. A product analysis is provided in Table 2.

EXAMPLE TWO

Laboratory pilot plant batches of the product are prepared by placing 37.9 kg (83.4 lbs) of water into a cooker tank. An agitator is turned on. Slowly, 12.9 kg (28.35 lbs) of whole-wheat flour was added while carefully observing that lumping of the slurry did not occur. A tight fitting top was applied and clamped down. Next, steam was injected into the tank. The tank temperature slowly rose to 32° C. (90° F.) and in 15.45 grams of BAN 120L brand alpha-amylase from NOVO Nordisk Bioindustrials Inc. of Danbury, Conn. was added to the slurry. The steam was adjusted as necessary to enable the slurry temperature to reach about 96° C. to 97° C. (204° F. to 206° F.) in one hour. Next, the slurry was held at about this approximately 96° C. (204° F.) temperature for 15 minutes. Approximately 3.6 kg (8 lbs) of the treated slurry was then drained into a stainless steel bucket. With an insert basket placed in the centrifuge and the centrifuge running at 1500 rpm the slurry was slowly poured into the centrifuge and allowed to spin for about three minutes. After five buckets had subsequently been run through the centrifuge, the cake from the centrifuge was placed in a hopper for a small lab drum dryer. The dryer's internal temperature was 174° C. to 177° C. (346° F. to 350° F.) due to connection to 120 psi steam. The external surface temperature on the drum dryer was approximately 154° C. to 160° C. (310° F. to 320° F.). With the drums turning and scrapers tightened to remove heat treated material from the drum dryer surface after traveling about ¾ of a revolution, the product was collected. Analysis of the thus collected product corresponds to the information provided in Table 2.

A comparison of the product of the present invention to other high fiber products is provided in Table 1. Note that in comparison to other high fiber bakery ingredients, the present invention shows a unique combination of low-fat and high-protein.

EXAMPLE THREE

A low-calorie (40 calorie per slice) bread according to the present invention was prepared according to the following formula:

| BAKERS PERCENT* | SPONGE INGREDIENT | |
|---|---|---|
| 60 | FOUR (CLEAR) | Mix 1 min low |
| 8 | VITAL WHEAT GLUTEN | 5 min second speed |
| 48 | WATER | Sponge should be |
| 2.5 | YEAST | 22° C.–23° C. |
| 0.375 | SODIUM STEAROYL LACTYLATE | (72–74° F.) 3 hr fermentation |
| 15 PPM | BROMATE | |

| BAKERS* PERCENT | DOUGH INGREDIENTS | |
|---|---|---|
| 40 | FLOUR (CLEAR) | MIX 3 min low |
| 75 | WATER (VARIABLE) | 9 min & speed (variable) |
| 3 | YEAST | Dough temp of |
| 3.5 | SALT | 25° C.–27° C. |
| 3 | GRANULATED SUGAR | (77°–80°) |
| 8 | VITAL WHEAT GLUTEN | |
| 6 | REG WHEAT STARCH | Allow 10 min floor time |
| 1 | MOLASSES | |
| 0.5 | CALCIUM PROPIONATE | Divide & give 7 min overhead proof |
| 0.75 | CALCIUM SULFATE | |
| 1 | OIL | Mould, proof to |

-continued

| | | |
|---|---|---|
| 0.3 | ETHOXYLATED MONO-DIGLYCERIDES & MONO-DIGLYCERIDES | height (¾") Bake 20 min at |
| 30 PPM | AZODICARBONAMIDE | 455° F. |
| 45 PPM | BROMATE | |
| 295.175 | | |

*Baker's percent is based on 100 lbs of flour.

The bread was baked, cooled, sliced and bagged one hour after removal from the oven. Two commercial breads Wonder Light Bread from Continental Baking Company, Inc. and Colonial Light Wheat Bread from Campbell Taggert, Inc. were purchased two days from their bake date. Penetrometer testing was done on the 2nd, 4th, 6th, 8th and 10th days after baking. The test methodology for the penetrometer testing involved placing four slices of bread on a penetrometer base and adjusting the shaft such that the weight just touches the top slice of bread. A total weight of 270 grams is allowed to drop freely and apply pressure to the bread for 1 minute. Readings of penetration into the bread after 1 minute are observed in 32ths of an inch. Greater depths of penetration are indicative of softer crumb and weaker crumb structure. The results are presented in Table 3.

The results demonstrate superior crumb strength and structure in a low-calorie, high-protein, high-fiber bread of the present invention relative to well-known commercial low-calorie breads. The superior crumb structure continued over the 10-day test period.

Although the present invention has been described with reference to the preferred embodiments, workers skilled in the art will recognize that changes may be made in form and detail without departing from the spirit and scope of the invention. Specifically, while the invention has been described in terms of the preferred embodiment in which maltose is the preferred preselected sugar, it is envisioned by the inventor that other sugars, for example, fructose or glucose, might be desired; thus, the enzyme preparation and system employed would be changed to generate such alternative preselected sugars. It is within the skill of the art to modify the conditions of enzymatic digest temperature, duration and concentration of enzyme and substrate and additionally, to modify the temperature and duration of the heating step in order to provide appropriate caramelization. Such modifications are envisioned by the inventor as within the scope of the present invention.

TABLE 1

| Product | TDF | Color | Flavor | Fat | Protein |
|---|---|---|---|---|---|
| Present Invention | 32–35% | Tan | Wheaty/ Nutty | <6% | 26–30% |
| Oat Hull Fiber | 90% | Cream | bland | .3% | <1% |
| Rice Bran | 20–30% | Caramel | Sweet/ Nutty | 16–30% | 12% |
| Soy Hull Fiber | 92% | White | Tasteless | .6% | 9% |
| Yellow Corn Bran | 90% | Light Tan | Bland | 1% | 6% |
| Wood Pulp Cellulose | 99% | White | Bland | <1% | <1% |

TABLE 2

| PRODUCT ANALYSIS | |
|---|---|
| FAT % | 3.0–6% |
| PROTEIN | 26–30% |
| Total Dietary Fiber | 32–35% |
| Moisture | Maximum 5.5% |

TABLE 2-continued

| NUTRITIONAL INFORMATION | |
|---|---|
| Protein g. | 26.02 |
| Fat, g. | 6 |
| Carbohydrates, g. | 27.69 |
| Calories | 270 |
| Sodium, mg. | 32.5 |
| Calcium, mg. | 283 |
| Iron, mg. | 10.33 |
| Total Sugars, g. | 16.4 |
| MICROBIOLOGICAL | |
| Total Plate Count | Maximum 10,000/g. |
| E. Coli and Salmonella | both Negative |
| SHELF LIFE | |
| Recommended 6 months. | |
| Store at room temperature. | |

TABLE 3

| CRUMB STRUCTURE | | | |
|---|---|---|---|
| | Example 3 | Wonder | Colonial |
| Day 2 | 24.25 | 31.5 | 28.25 |
| Day 4 | 23.25 | 28.75 | 30.25 |
| Day 6 | 19.25 | 28.25 | 24.60 |
| Day 8 | 19.25 | 26.50 | 25.25 |
| Day 10 | 19.25 | 26.00 | 25.25 |

What is claimed is:

1. A baking ingredient comprises:
   milled, starch-bearing cereal grain having about 60-80% of the starch enzymatically converted to a soluble form, and about 4-30% by weight of a caramel-sugar mixture, said sugars of said mixture comprising at least 70% maltose and less than 5% glucose and wherein the starch bearing cereal grain is wheat.

2. The baking ingredient of claim 1 and wherein the grain is treated with alpha-amylase.

3. The baking ingredient of claim 2 and wherein the alpha-amylase is thermally denatured when 60-80% of the starch has been converted to a soluble form.

4. The baking ingredient of claim 3 and wherein the alpha-amylase is a bacterial alpha-amylase preparation having substantially no maltase activity.

5. A baking ingredient comprising:
   milled, starch-bearing cereal grain having about 60-80% of the starch enzymatically converted to a soluble form, and about 4-30% by weight of a caramel-sugar mixture, said sugars of said mixture comprising at least 70 maltose and less than 5% glucose and wherein the ingredient has about 70-75% of the original starch of the cereal grain converted to a soluble form.

6. The baking ingredient of claim 5 and wherein the ingredient is further characterized by a protein content of about 26-30%.

7. The baking ingredient of claim 5 and wherein the ingredient is further characterized by a total dietary fiber content of about 32-35%.

8. The baking ingredient of claim 5 and wherein the source of the sugar of the caramel-sugar mixture is the enzymatically converted solubilized starch of the cereal grain.

9. The baking ingredient of claim 5 and wherein the source of the caramel of the caramel-sugar mixture is the thermal caramelization of the sugars produced by enzymatically converted solubilized starch of the cereal grain.

10. A baking ingredient comprising:
    milled, starch-bearing cereal grain having about 60-80% of the starch enzymatically converted to a soluble form, and about 4-30% by weight of a caramel-sugar mixture, said sugars of said mixture comprising at least 70% maltose and less than 5% a glucose and wherein the ingredient is substantially free of sugar crystals of a size capable of mechanically damaging a yeast-raised dough.

11. A baking premix comprising a bakery ingredient comprising:
    milled, starch-bearing cereal grain having about 60-80% of the starch enzymatically converted to a soluble form, and about 4-30% caramel-sugar mixture, said sugars of said mixture comprising at least 70% maltose and less than 5% glucose.

12. A baked good for human consumption prepared from a dough comprising a bakery ingredient comprising:
    milled, starch-bearing cereal grain having about 60-80% of the starch enzymatically converted to a soluble form, and about 4-30% by weight of caramel sugar mixture, said sugars of said mixture comprising at least 70% maltose and less than 5% glucose.

13. A process for preparing a bakery ingredient comprising the steps of:
    suspending a milled grain in aqueous media;
    enzymatically solublizing a substantial portion of the starch of the milled grain;
    terminating the enzymatic solubilization of starch when between about 60-80% of the original starch of the milled grain is solubilizied;
    separating the suspended starch depleted milled grain from a substantial fraction of the aqueous media incorporating solubilized starch; and
    heating the separated grain in the presence of the remaining fraction of the aqueous media incorporating solubilized starch
    and wherein the heating step occurs at a temperature and for a time sufficient to caramelize a portion of the solubilized starch.

14. The process of claim 13 and wherein the heating step results in a product with a moisture content of between about 2-9% moisture.

15. The process of claim 13 and wherein the step of enzymatically solubilizing includes exposure to alpha-amylase and causes the production of maltose and the heating step results in caramelization of from about 30-50% of the maltose in the remaining fraction of the aqueous media incorporating the maltose.

16. The process of claim 15 and wherein the enzymatically solubilizing step involving alpha-amylase causes the production of a sugar profile with more than 90% maltose and less than 5% glucose.

17. A process for preparing a bakery ingredient comprising the steps of:
    suspending a milled grain in aqueous media;
    enzymatically solubilized a substantial portion of this starch of the milled grain;
    terminating the enzymatic solubilization of starch when between about 60-80% of the original starch of the milled grain is solubilized;
    separating the suspended starch depleted milled grain from a substantial fraction of the aqueous media incorporating solubilized starch; and
    heating the separated grain in the presence of the remaining fraction of the aqueous media incorporating solubilized starch to form a product containing from 2-10% moisture and further comprising the step of mixing the suspension of milled grain prior to the separation step to provide a substantially homogeneous separated grain in the presence of remaining fraction of aqueous media incorporating solubilized starch for the heating step.

18. A process for preparing a bakery ingredient comprising the steps of:

suspending a milled grain in aqueous media;

enzymatically solubilizing a substantial portion of the starch of the milled grain;

terminating the enzymatic solubilization of starch when between about 60-80% of the original starch of the milled grain is solubilized;

separating the suspended starch depleted milled grain from a substantial fraction of the aqueous media incorporating solubilized starch to form a product containing from 2-10% moisture; and heating the separate grain in the presence of the remaining fraction of the aqueous media incorporating solubilized starch and further comprising the step of:

blending the product resulting from the heating step.

19. A process for preparing a bakery ingredient comprising the steps of:

suspending a milled grain in aqueous media;

enzymatically solublizing a substantial portion of the starch of the milled grain;

terminating the enzymatic solubilization of starch when between about 60-80% of the original starch of the milled grain is solubilized;

separating the suspended starch depleted milled grain from a substantial fraction of the aqueous media incorporating solubilized starch to form a product containing from 2-10% moisture; and heating the separated grain in the presence of the remaining fraction of the aqueous media incorporating solubilized starch;

and further comprising the step of:

selecting an enzyme preparation to convert the starch of the milled grain to a preselected sugar composition.

20. The process of claim 19 and wherein the enzyme preparation consists essentially of a bacterial alpha-amylase substantially free of maltase activity and the selected sugar composition includes at least 70% maltose and less than 5% glucose.

21. A baking ingredient comprising:

milled, starch-bearing cereal grain having about 60-80% of the starch enzymatically eliminated and converted to a pre-selected sugar composition, and about 4-30% by weight of a mixture of caramel and the pre-selected sugar composition.

22. The baking ingredient of claim 21 and wherein the preselected sugar composition includes at least 70% maltose and less than 5% glucose.

23. A high-fiber and protein food product comprising:

a particle consisting essentially of the vestige of alpha-amylase digested, gelatinized, milled, starch-bearing cereal grain; and an intimately associated portion consisting essentially of partially caramelized maltose.

24. A dough composition comprising a bakery ingredient comprising:

milled, starch-bearing cereal grain having about 60-80% of the starch enzymatically converted to a soluble form, and about 4-30% by weight of caramel-sugar mixture, said sugars of said mixture comprising at least 70% maltose and less than 5% glucose.

* * * * *